US008173850B2

(12) United States Patent
Furuya et al.

(10) Patent No.: US 8,173,850 B2
(45) Date of Patent: May 8, 2012

(54) ALKANEDIOL COMPOSITION, PROCESS FOR PRODUCING THE SAME, AND COSMETIC

(75) Inventors: Masaki Furuya, Tokyo (JP); Yasuhiro Tsushima, Tokyo (JP); Kimiyoshi Namiwa, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 13/213,854

(22) Filed: Aug. 19, 2011

(65) Prior Publication Data

US 2011/0301389 A1 Dec. 8, 2011

Related U.S. Application Data

(62) Division of application No. 11/912,698, filed as application No. PCT/JP2006/308652 on Apr. 25, 2006, now abandoned.

(30) Foreign Application Priority Data

Apr. 28, 2005 (JP) ................................. 2005-133200

(51) Int. Cl.
*C07C 27/00* (2006.01)
*A61K 8/00* (2006.01)

(52) U.S. Cl. ........................................ 568/867; 510/119
(58) Field of Classification Search ......................... None
See application file for complete search history.

(56) References Cited

U.S. PATENT DOCUMENTS

| 4,551,566 A * | 11/1985 | Robson et al. | 568/867 |
| 4,605,795 A | 8/1986 | Siegmeier et al. | |
| 4,760,200 A * | 7/1988 | Keen et al. | 568/867 |
| 5,345,004 A | 9/1994 | Nishiguchi | |
| 6,201,159 B1 | 3/2001 | Choi et al. | |
| 6,528,665 B1 | 3/2003 | Cheng et al. | |
| 2004/0142177 A1* | 7/2004 | Verborgt et al. | 428/413 |

FOREIGN PATENT DOCUMENTS

| EP | 1437337 A1 | 7/2004 |
| JP | 57-062234 A | 4/1982 |
| JP | 60-078928 A | 5/1985 |
| JP | 61-065834 A | 4/1986 |
| JP | 61-130247 A | 6/1986 |
| JP | 07-010789 A | 1/1995 |
| JP | 2000-505103 A | 4/2000 |
| JP | 2003-096006 | 4/2003 |
| JP | 2003-238466 A | 8/2003 |
| JP | 2004-115404 A | 4/2004 |
| JP | 2004-189636 A | 7/2004 |

OTHER PUBLICATIONS

Letter from McHale & Slavin dated Jul. 8, 2011.
W.H. Pirkle, et al., "Direct Chromatographic Separation of Enantiomeric Diol Derivatives," Journal of Chromatography, 388 (1987) pp. 307-314.
P.C. Schmid, et al., "15-Methyl-1,2-hexadecanediol, a Major Constituent of Hamster Surface Wax," Lipids, vol. 13 (1978), No. 11, pp. 825-827.
U. Sundermeier, et al., Modern Oxidation Methods, "Chapter 1. Recent Developments in the Osmium-catalyzed Dihydroxylation of Olefins," pp. 1-2 (2004 Wiley-VCH).
P.C. Bandi, et al., "Configurational Analysis of Long-Chain Alkanediols," Chemistry and Physics of Lipids 17 (1976) pp. 267-274.
L.C. Branco, et al., "Catalytic Asymmetric Dihydroxylation of Olefins Using a Recoverable and Reusable OsO42—in Ionic Liquid [bmin][PF6]" The Royal Society of Chemistry (2002).
S.P. Verevkin, "Determination of Vapor Pressures and Enthalpies of Vaporization of 1,2-alkanediols," Fluid Phase Equilibria 224 (2004) pp. 23-29.
Japanese Patent Office, "Notice of Reasons for Refusal," issued in connection with Japanese Patent Application No. 2007-514746, dated Feb. 24, 2012.

* cited by examiner

*Primary Examiner* — Patricia A Duffy
*Assistant Examiner* — Garen Gotfredson
(74) *Attorney, Agent, or Firm* — Sughrue Mion, PLLC

(57) ABSTRACT

A less malodorous alkanediol composition, a process for producing the alkanediol composition efficiently, and a cosmetic containing the alkanediol composition are provided. An alkanediol composition contains 0.005 parts by mass or less of ester compound per 100 parts by mass of alkanediol compound having four or more carbon atoms. An alkanediol composition contains 0.2 parts by mass or less of dioxane compound per 100 parts by mass of alkanediol compound having four or more carbon atoms. Furthermore, an ether-containing dihydric alcohol is preferably 0.3 parts by mass or less per 100 parts by mass of alkanediol compound.

2 Claims, No Drawings

ALKANEDIOL COMPOSITION, PROCESS FOR PRODUCING THE SAME, AND COSMETIC

CROSS-REFERENCE TO RELATED APPLICATIONS

This application is a divisional of U.S. application Ser. No. 11/912,698 filed Oct. 26, 2010, which is a National Stage Entry of PCT/JP2006/308652 filed Apr. 25, 2006, which claims priority benefit to Japanese Application No. 2005-133200 filed Apr. 28, 2005, the disclosures of each of which are incorporated herein by reference.

TECHNICAL FIELD

The present invention relates to an alkanediol composition, a process for producing the alkanediol composition, and a cosmetic, and more particularly to an alkanediol composition that contains little specific by-products and that generates no unpleasant smell, a process for producing the alkanediol composition, and a cosmetic.

BACKGROUND ART

It is unavoidable for manufacturers of organic compounds that organic chemical reactions are associated with the formation of by-products. The amount of by-product is often much smaller than that of end product. However, even a small amount of by-product sometimes chemically affects an end product, for example, by worsening the color or smell of the end product. For manufacturers of organic compounds, preventing the formation of disadvantageous by-products or finally removing disadvantageous by-products to prevent these adverse effects is part of manufacturing processes.

In such a situation, alkanediol compounds have been used in various applications, such as cosmetic preservatives and humectants, pearling agents, raw materials for synthetic fiber, raw materials for urethane compounds, and water-based inks. However, particularly in cosmetic applications, the smell of alkanediol compounds formulated in products causes a big problem. For example, the addition of an alkanediol compound to a product free from a perfume impairs the unscented product. Even in a product containing a perfume, the addition of a malodorous alkanediol compound changes the smell of the product. Hence, there has been a great demand for an odorless or less malodorous alkanediol composition in cosmetic applications.

A currently common process for producing an alkanediol composition includes oxidizing an olefin with an oxidizing agent such as hydrogen peroxide to produce an epoxy compound and hydrolyzing the epoxy compound. Because an alkanediol composition thus produced has a smell, the alkanediol composition is usually purified by distillation, which is a common purification method (see Patent Documents 1 and 2, for example).

Patent Document 1: Japanese Unexamined Patent Application Publication No. 57-62234
Patent Document 2: Japanese Unexamined Patent Application Publication No. 60-78928

DISCLOSURE OF INVENTION

Problems to be Solved by the Invention

However, as described in Patent Document 1 or 2, alkanediol compositions have a smell even after distillation. This is because a component causing a smell is not identified, and the distillation is performed without knowing the component to be removed. Accordingly, it is an object of the present invention to provide a less malodorous alkanediol composition, a process for producing the alkanediol composition efficiently, and a cosmetic containing the alkanediol composition.

Means for Solving the Problems

As a result of diligent investigations on the above-mentioned problems, the present inventors identified a specific component causing a smell in an alkanediol composition and perfected the present invention by discovering that a less malodorous alkanediol composition can be produced by reducing the specific compound to a certain level.

Thus, an alkanediol composition according to the present invention contains 0.005 parts by mass or less of ester compound (A) per 100 parts by mass of alkanediol compound having four or more carbon atoms.

Furthermore, another alkanediol composition according to the present invention contains 0.2 parts by mass or less of dioxane compound (C) per 100 parts by mass of alkanediol compound having four or more carbon atoms.

Furthermore, in the present invention, an ether-containing dihydric alcohol (B) is preferably 0.3 parts by mass or less per 100 parts by mass of alkanediol compound.

Furthermore, an alkanediol compound having a general formula (1) can suitably be used in the present invention:

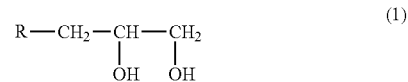

wherein R denotes an alkyl group having 4-15 carbon atoms. Furthermore, the alkanediol compound is preferably a hydrolysate of an epoxy compound produced by an oxidation reaction of an olefin.

Furthermore, a process for producing an alkanediol composition according to the present invention includes the steps of (a) oxidizing an olefin to produce an epoxy compound, (b) hydrolyzing the epoxy compound to produce the alkanediol composition, and (c) adding water and/or an organic solvent to the alkanediol composition and removing water and/or the organic solvent under reduced pressure.

A cosmetic according to the present invention contains an alkanediol composition according to the present invention.

Advantages of the Invention

An alkanediol composition according to the present invention has little smell. Furthermore, cosmetics containing an alkanediol composition according to the present invention do not have any problem caused by the smell of the alkanediol composition. An alkanediol composition containing a low concentration of component causing a smell can efficiently be produced by a process for producing an alkanediol composition according to the present invention.

BEST MODE FOR CARRYING OUT THE INVENTION

An alkanediol compound that can be used in the present invention has at least four carbon atoms. In addition, any two hydrogen atoms of a saturated aliphatic hydrocarbon of the alkanediol compound are replaced by hydroxyl groups. Examples of the alkanediol compound include 1,2-butanediol, 1,3-butanediol, 1,4-butanediol, 1,5-pentanediol, neopentyl glycol, isoprene glycol (3-methyl-1,3-butanediol), 1,2-hexanediol, 1,6-hexanediol, 3-methyl-1,5-pentanediol, 1,2-octanediol, 2,3-octanediol, 2-ethyl-1,3-hexanediol, 2-butyl-2-ethyl-1,3-propanediol, 2,5-dimethyl-2,5-hexanediol, 1,2-decanediol, 1,2-dodecanediol, 1,2-tetradecanediol, 1,2-hexadecanediol, 1,2-octadecanediol, 1,12-octadecanediol, 1,2-cyclohexanediol, 1,4-cyclohexanediol, and 1,4-cyclohexanedimethanol.

Among others, vicinal compounds that have two hydroxyl groups on adjacent carbon atoms are preferred. Compounds having a general formula (1) are more preferred:

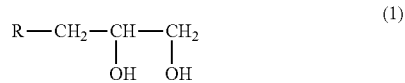

(1)

wherein R denotes an alkyl group having 4-15 carbon atoms. Examples of the alkyl group include a butyl group, an isobutyl group, a secondary butyl group, a tertiary butyl group, a pentyl group, an isopentyl group, a secondary pentyl group, a neopentyl group, a tertiary pentyl group, a hexyl group, a secondary hexyl group, a heptyl group, a secondary heptyl group, an octyl group, a secondary octyl group, a nonyl group, a secondary nonyl group, a decyl group, a secondary decyl group, an undecyl group, a secondary undecyl group, a dodecyl group, a secondary dodecyl group, a tridecyl group, an isotridecyl group, a secondary tridecyl group, a tetradecyl group, a secondary tetradecyl group, a hexadecyl group, a secondary hexadecyl group, a stearyl group, a 2-ethylhexyl group, a 2-butyloctyl group, a 2-butyldecyl group, and a 2-hexyloctyl group.

The alkyl groups preferably have 4-9 carbon atoms, more preferably 4-7 carbon atoms, still more preferably 4-6 carbon atoms, and most preferably 5 carbon atoms.

While an alkanediol composition according to the present invention may be produced by any process, the alkanediol composition may be produced by oxidizing an olefin into an epoxy compound and subsequently hydrolyzing the epoxy compound. The olefin may be oxidized with an oxidizing agent, such as hydrogen peroxide, a peroxide compound, or an inorganic oxidizing agent. The epoxy compound may be hydrolyzed by a direct reaction with water under high pressure or by a reaction between the epoxy compound and formic acid or acetic acid, followed by hydrolysis with an alkaline substance. Alkanediol compositions thus produced always contain by-products, such as ester compounds, unsaturated alcohols, or acetal compounds. However, compounds causing smells have not been identified. Thus, alkanediol compositions are usually purified by distillation, which is a common purification method, as described above. However, smells of the alkanediol compositions cannot be removed by distillation alone.

As a result of investigations, the present inventors found that ester compounds and dioxane compounds have the largest influence on the smell among compounds causing smells. In an alkanediol composition according to a first embodiment of the present invention, therefore, the content of an ester compound (A) must be 0.005 parts by mass or less per 100 parts by mass of alkanediol compound. The term "ester compound (A)" means a compound having an ester bond and includes reaction products between epoxy compounds and fatty acids, such as formic acid and acetic acid, reaction products between alkanediol compounds and fatty acids, and reaction products between compounds having a carbonyl group, which are produced by the oxidation of olefins, and epoxy compounds or alkanediol compounds. These ester compounds cause a smell. Hence, the content of an ester compound in an alkanediol composition according to the present invention is 0.005 parts by mass or less, preferably 0.003 parts by mass or less, and more preferably 0.001 parts by mass or less per 100 parts by mass of alkanediol compound. More than 0.005 parts by mass of ester compound (A) in an alkanediol composition causes an unpleasant smell.

In an alkanediol composition according to a second embodiment of the present invention, the content of a dioxane compound (C) must be 0.2 parts by mass or less per 100 parts by mass of alkanediol compound. In the present invention, reduction in the amount of dioxane compound (C) can also reduce a smell. Examples of the dioxane compound (C) include compounds having general formulae (2) and (3) (wherein R is as defined above). The dioxane compound (C) may be produced by a dehydration condensation reaction of alkanediols or a condensation reaction of unreacted epoxy compounds. The content of the dioxane compound (C) in an alkanediol composition according to a second embodiment of the present invention is 0.2 parts by mass or less, preferably 0.15 parts by mass or less, and more preferably 0.1 parts by mass or less per 100 parts by mass of alkanediol compound. More than 0.2 parts by mass of dioxane compound (C) in an alkanediol composition causes an unpleasant smell.

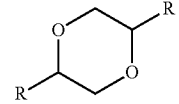

(2)

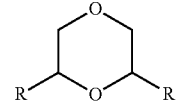

(3)

In the present invention, as described above, reduction of the content of either the ester compound (A) or the dioxane compound (C) leads to a less malodorous alkanediol composition. Another by-product causing a smell of an alkanediol composition is an ether-containing dihydric alcohol. Examples of the ether-containing dihydric alcohol (B) include compounds having general formulae (4), (5), and (6) (wherein R is as defined above). The ether-containing dihydric alcohol (B) may be produced by a dehydration condensation reaction of alkanediols. The content of the ether-containing dihydric alcohol (B) in an alkanediol composition according to the present invention is preferably 0.3 parts by mass or less, more preferably 0.2 parts by mass or less, and still more preferably 0.15 parts by mass or less per 100 parts by mass of alkanediol compound. More than 0.3 parts by mass of ether-containing dihydric alcohol (B) in an alkanediol composition causes an unpleasant smell.

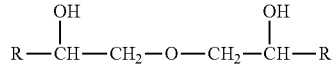

(4)

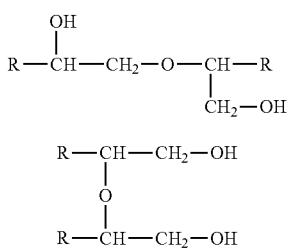

Such a by-product may be analyzed by a method using an analyzer, such as gas chromatography, liquid chromatography, a mass spectrometer, NMR, or IR, or by titration analysis of a saponification value, the degree of unsaturation, or a hydroxyl value. In terms of microanalysis of a by-product, the by-product may be analyzed preferably by instrumental analysis, more preferably by gas chromatography or with a mass spectrometer, and still more preferably by gas chromatography. In an alkanediol composition according to the present invention, because the peak area ratio in a gas chromatography chart indicates the mass ratio, the mass ratio of each component can easily be determined.

Gas chromatography analysis may be performed under any condition under which a by-product can be separated. Exemplary conditions are as follows: a gas chromatograph GC-14B (Shimadzu Corporation) with a J & W Scientific DB-1 column (100% dimethylpolysiloxane, inner diameter 0.53 mm, length 15 m, film thickness 1.5 μm); a 20 ml/min nitrogen carrier gas; an FID detector temperature of 320° C.; an air pressure of 50 kPa; a hydrogen pressure of 50 kPa; and a vaporization chamber temperature of 320° C. The column may be held at 60° C. for five minutes, be heated to 280° C. at 10° C./min, and be held at 280° C. for three minutes. 0.1 μl of sample diluted to 1.5% by weight in ethanol may be injected with a microsyringe.

Under the conditions described above, a main peak of 1,2-octanediol appears at a retention time of about 10 min. A peak of a by-product, if any, appears before or after the main peak. The peak area ratio indicates the mass ratio of each component. A peak of an ester compound appears zero to two minutes before the retention time of the main peak. A peak of a dioxane compound appears four to seven minutes after the retention time of the main peak. A peak of an ether-containing dihydric alcohol appears eight to fifteen minutes after the retention time of the main peak.

In an alkanediol composition according to a first embodiment of the present invention, the peak area of an ester compound appearing zero to two minutes before the retention time of the main peak must be 0.005% or less, preferably 0.003% or less, and more preferably 0.001% or less of the main peak area. When the peak area of an ester compound exceeds 0.005% of the main peak area, the content of the ester compound exceeds 0.005 parts by mass per 100 parts by mass of alkanediol compound. A component causing a smell and having an unknown structure may appear zero to two minutes after the retention time of the main peak. A peak in this area is therefore indicative of a strong smell and is not preferred.

In an alkanediol composition according to a second embodiment of the present invention, the peak area of a dioxane compound appearing four to seven minutes after the retention time of the main peak must be 0.2% or less, preferably 0.15% or less, and more preferably 0.1% or less of the main peak area. When the peak area of a dioxane compound exceeds 0.2% of the main peak area, the content of the dioxane compound exceeds 0.2 parts by mass per 100 parts by mass of alkanediol compound.

The peak area of an ether-containing dihydric alcohol appearing eight to fifteen minutes after the retention time of the main peak is preferably 0.3% or less, more preferably 0.2% or less, and still more preferably 0.15% or less of the peak area of the main peak. When the peak area of an ether-containing dihydric alcohol exceeds 0.3% of the main peak area, the content of the ether-containing dihydric alcohol exceeds 0.3 parts by mass per 100 parts by mass of alkanediol compound. This may cause a smell.

An alkanediol composition according to the present invention may be produced by any known method that can reduce an ester compound by-product to 0.005 parts by mass or less, and/or that can reduce a dioxane compound by-product to 0.2 parts by mass or less, per 100 parts by mass of alkanediol compound. As described above, the content of ester compound and/or the content of dioxane compound cannot be reduced to the range described above by common distillation alone. A smell therefore cannot be removed. This is probably because the boiling points of the components causing a smell, that is, an ester compound and a dioxane compound, are very close to the boiling point of the alkanediol compound.

Examples of a purification method used in the production of an alkanediol composition according to the present invention include azeotropic distillation of by-products and a large amount of water under reduced pressure; azeotropic distillation of by-products and an organic solvent under reduced pressure; azeotropic distillation of by-products, water, and an organic solvent under reduced pressure; blowing of water vapor under reduced pressure; adsorption of by-products on an adsorbent, such as an ion exchange resin or activated carbon, and subsequent distillation; recrystallization in a solvent, such as ethanol, acetone, or hexane; and combinations thereof; and combinations of these methods and known purification methods.

Among others, blowing of water vapor under reduced pressure; azeotropic distillation of by-products and water and/or an organic solvent under reduced pressure (this is a method according to the present invention); and the addition of an organic solvent and blowing of water vapor under reduced pressure are preferred, because an ester compound causing a smell can efficiently be removed by these methods.

In the blowing of water vapor, the total amount of water is preferably in the range of 30 to 200 parts by mass, more preferably in the range of 50 to 150 parts by mass, and still more preferably in the range of 50 to 100 parts by mass per 100 parts by mass of alkanediol composition. The distillation temperature is preferably in the range of 80° C. to 120° C., more preferably in the range of 85° C. to 110° C., and still more preferably in the range of 90° C. to 100° C. The degree of vacuum is preferably 10 kPa or less, more preferably 5 kPa or less, and still more preferably 1.3 kPa or less.

The amount of the organic solvent is preferably in the range of 30 to 200 parts by mass, more preferably in the range of 50 to 150 parts by mass, and still more preferably in the range of 80 to 120 parts by mass per 100 parts by mass of alkanediol composition. Furthermore, the organic solvent may be added in a plurality of portions. For example, the addition and removal of 10 parts by mass of organic solvent may be repeatedly performed. In the addition of the organic solvent in a plurality of portions, the total amount of the organic solvent is preferably in the range as described above.

The amount of water is preferably in the range of 30 to 200 parts by mass, more preferably in the range of 50 to 150 parts by mass, and still more preferably in the range of 80 to 120 parts by mass per 100 parts by mass of alkanediol composition. Furthermore, water may be added in a plurality of portions. For example, the addition and removal of 10 parts by mass of water may be repeatedly performed. In the addition of water in a plurality of portions, the total amount of water is preferably in the range as described above. The degree of vacuum is preferably 10 kPa or less, more preferably 5 kPa or less, and still more preferably 1.3 kPa or less.

When an organic solvent and water, or an organic solvent and water vapor, are combined, preferably 20-150 parts by mass, more preferably 30-100 parts by mass of water or water vapor per 100 parts by mass of organic solvent is added or blown. The total amount of the organic solvent and water or the total amount of the organic solvent and water vapor is preferably in the range of 50 to 300 parts by mass, more preferably in the range of 80 to 250 parts by mass, and still more preferably in the range of 100 to 200 parts by mass per 100 parts by mass of alkanediol composition. The degree of vacuum is preferably 10 kPa or less, more preferably 5 kPa or less, and still more preferably 1.3 kPa or less.

Examples of organic solvent for use in the purification method include glycol compounds, such as ethylene glycol, propylene glycol, butylene glycol, diethylene glycol, dipropylene glycol, methyl cellosolve, ethyl cellosolve, propyl cellosolve, butyl cellosolve, propylene glycol monomethyl ether, and diethylene glycol monomethyl ether; acyclic hydrocarbons, such as hexane, octane, nonane, and decane; and aromatic hydrocarbons, such as benzene, toluene, xylene, trimethylbenzene, cumene, and naphthalene. Among others, in terms of removal of by-products, glycol solvents are preferred, propylene glycol, dipropylene glycol, and diethylene glycol are more preferred, and propylene glycol is most preferred.

If necessary, another component may be added to an alkanediol composition according to the present invention within the limits not compromising the advantages of the present invention. Examples of the additive component include water; surfactants, such as nonionic surfactants, anionic surfactants, cationic surfactants, and amphoteric surfactants; antioxidants; light stabilizers; silicone oils; thickeners; oil solutions; powders (pigments, dyes, and resins); preservatives; perfumes; humectants; bioactive components; salts; solvents; antioxidants; chelating agents; counteractives; pH adjusters; enzymes; and cyclic oligosaccharides such as cyclodextrins.

An alkanediol composition according to the present invention may be allowed to react with another compound reactive with a hydroxyl group. Examples of the compound reactive with a hydroxyl group include isocyanate compounds, epoxy compounds, and compounds containing carboxylic acids such as fatty acids. An alkanediol composition according to the present invention may be allowed to react with these compounds and thereby be included in urethane resins, epoxy resins, and polyesters. Furthermore, because an alkanediol composition according to the present invention contains only a small amount of by-products, few side reactions occur, and a final product advantageously contains only a small amount of by-products.

A cosmetic according to the present invention contains an alkanediol composition according to the present invention. In the cosmetic, the alkanediol composition may be used as a humectant or a preservative, or a pearling agent in a shampoo. Examples of the cosmetic include facial cleansing creams, cleansing foams, cleansing creams, cleansing milks, cleansing lotions, massage creams, cold creams, moisture creams, sun blocks, body shampoos, hair shampoos, hair rinses, hair treatments, hair-restorers, hair creams, hair lacquers, setting lotions, hair bleaches, color rinses, permanent wave lotions, hand creams, lipsticks, packs, foundations, toilet water, cosmetic liquid, milky lotions, colognes, bath cosmetics, kitchen detergents, laundry detergents, bath detergents, nail cosmetics, and tooth powders.

EXAMPLES

The present invention will be further illustrated with examples below.

Production of Diol Compound

Production Example 1

Production of Octanediol 381 g (3.4 mol) of α-olefin having eight carbon atoms and 218 g (4.5 mol) of 95% formic acid were charged into a 2000 ml four-neck glass flask with a stirrer, a thermometer, and a nitrogen inlet. Then, 261 g (4.6 mol) of 60% hydrogen peroxide was added dropwise at 60° C. for two hours. After the completion of dropping, the reactant was aged at 60° C. for eight hours. After the reactant was left to stand and a lower aqueous layer was removed, 192 g (1.2 mol) of 25% aqueous sodium hydroxide was added to the reactant. The reactant was stirred at 60° C. for 30 minutes for saponification and was left to stand. A lower aqueous layer was then removed. After the saponification and removal of the aqueous layer were performed one more time, the product was washed with hot water and hexane to yield 380 g of 1,2-octanediol.

Production Example 2

Production of Decanediol

As in Production Example 1, 1,2-decanediol was produced from an α-olefin having 10 carbon atoms.

Production Example 3

Production of Dodecanediol

As in Production Example 1, 1,2-dodecanediol was produced from an α-olefin having 12 carbon atoms.

Purification

Treatment 1

A hundred grams of diol compound produced in Production Example 1, 2, or 3 and 100 g of propylene glycol were charged into a 500 ml four-neck glass flask with a stirrer, a thermometer, and a nitrogen inlet. The reactant was heated to 90° C. to 95° C. Propylene glycol was then completely removed at a reduced pressure of 1.33 kPa to yield a purified diol compound.

Treatment 2

A hundred grams of diol compound produced in Production Example 1, 2, or 3, 100 g of propylene glycol, and 50 g of water were charged into a 500 ml four-neck glass flask with a stirrer, a thermometer, and a nitrogen inlet. The reactant was heated to 90° C. to 95° C. Propylene glycol was then completely removed at a reduced pressure of 1.33 kPa to yield a purified diol compound.

Treatment 3

A hundred grams of diol compound produced in Production Example 1, 2, or 3 was charged into a 300 ml four-neck glass flask with a stirrer, a thermometer, and a nitrogen inlet. The reactant was distilled at a temperature in the range of 120° C. to 180° C. and a reduced pressure in the range of 1.4 to 1.8 kPa to yield a purified diol compound as a main fraction.

Treatment 4

Fifty grams of diol compound produced in Production Example 1, 2, or 3 and 10 g of activated carbon were charged into a 200 ml beaker and were stirred at 50° C. After two hours, the activated carbon was filtered out to yield a purified diol compound.

The purified diol compounds thus produced were analyzed by gas chromatography under conditions described below. Peak areas were calculated to determine the amounts of impurities. The amounts of impurities were expressed as ratios of peak area to that of the main peak (diol compound), which was set to be 100. Tables 1 to 3 show the results for 1,2-octanediol (Production Example 1), 1,2-decanediol (Production Example 2), and 1,2-dodecanediol (Production Example 3), respectively.

Analyzer: GC-14B (Shimadzu Corporation)
Column: DB-1 (J & W Scientific, 100% dimethylpolysiloxane, inner diameter 0.53 mm, length 15 m, film thickness 1.5 μm)
Carrier gas: Nitrogen, 20 ml/min
Air pressure: 50 kPa
Hydrogen pressure: 50 kPa
Temperature of vaporization chamber: 320° C.
Heating rate: held at 60° C. for five minutes, heated to 280° C. at 10° C./min, and held at 280° C. for three minutes.
Sample amount: 0.1 μl (1.5% by weight in ethanol)

TABLE 1

| | Retention time (min) | | | | |
|---|---|---|---|---|---|
| | 8.3~10.2 | 10.3 | 10.4~12.3 | 14.3~17.3 | 18.3~25.3 |
| Treatment 1 | 0.003 | 100 | 0 | 0.16 | 0.29 |
| Treatment 2 | 0.001 | 100 | 0 | 0.03 | 0.25 |
| Treatment 3 | 0.03 | 100 | 0 | 0.29 | 0.41 |
| Treatment 4 | 0.13 | 100 | 0 | 0.32 | 0.48 |
| Untreated | 0.25 | 100 | 0.05 | 0.48 | 0.58 |
| Identified components | Ester compound | Diol compound | — | Dioxane compound | Ether-containing dihydric |

TABLE 2

| | Retention time (min) | | | | |
|---|---|---|---|---|---|
| | 11.1~13.0 | 13.1 | 13.2~15.1 | 17.1~20.1 | 21.1~28.1 |
| Treatment 1 | 0.006 | 100 | 0 | 0.18 | 0.32 |
| Treatment 2 | 0.002 | 100 | 0 | 0.04 | 0.23 |
| Treatment 3 | 0.05 | 100 | 0 | 0.30 | 0.42 |
| Treatment 4 | 0.14 | 100 | 0 | 0.33 | 0.51 |
| Untreated | 0.23 | 100 | 0.04 | 0.46 | 0.61 |
| Identified components | Ester compound | Diol compound | | Dioxane compound | Ether-containing dihydric alcohol alcohol |

TABLE 3

| | Retention time (min) | | | | |
|---|---|---|---|---|---|
| | 13.7~15.6 | 15.7 | 15.8~17.7 | 19.7~22.7 | 23.7~30.7 |
| Treatment 1 | 0.006 | 100 | 0 | 0.19 | 0.29 |
| Treatment 2 | 0.002 | 100 | 0 | 0.06 | 0.21 |
| Treatment 3 | 0.05 | 100 | 0 | 0.25 | 0.41 |
| Treatment 4 | 0.15 | 100 | 0 | 0.32 | 0.49 |
| Untreated | 0.21 | 100 | 0.03 | 0.45 | 0.6 |
| Identified components | Ester compound | Diol compound | — | Dioxane compound | Ether-containing dihydric alcohol |

Test Example 1

Alkanediol compounds in Treatments 1 to 4 and untreated alkanediol compounds were evaluated by ten panelists (five men and five women) for evaluation items described below. Table 4 shows the results.

TABLE 4

| | | Number of Panelists | | |
|---|---|---|---|---|
| | | ○ | Δ | x |
| Treatment 1 | 1,2-octanediol | 9 | 1 | 0 |
| | 1,2-decanediol | 8 | 2 | 0 |
| | 1,2-dodecanediol | 9 | 1 | 0 |
| Treatment 2 | 1,2-octanediol | 10 | 0 | 0 |
| | 1,2-decanediol | 10 | 0 | 0 |
| | 1,2-dodecanediol | 10 | 0 | 0 |
| Treatment 3 | 1,2-octanediol | 0 | 4 | 6 |
| | 1,2-decanediol | 0 | 3 | 7 |
| | 1,2-dodecanediol | 0 | 4 | 6 |
| Treatment 4 | 1,2-octanediol | 0 | 2 | 8 |
| | 1,2-decanediol | 0 | 1 | 9 |
| | 1,2-dodecanediol | 0 | 1 | 9 |
| Untreated | 1,2-octanediol | 0 | 0 | 10 |
| | 1,2-decanediol | 0 | 0 | 10 |
| | 1,2-dodecanediol | 0 | 0 | 10 |

○: No smell.
Δ: A little smell but not unpleasant.
x: Unplesant smell.

These results show that, in gas chromatography, a large peak (ester compound) at zero to two minutes before the peak of a diol compound and/or a large peak (dioxane compound) at four to seven minutes after the peak of the diol compound are indicative of an unpleasant smell.

Test Example 2

1,2-octanediol in Production Example 1 was purified by the method described in Treatment 2. Shampoos were prepared with the purified 1,2-octanediol and untreated 1,2-octanediol according to the formula shown in Table 5. The two shampoos were evaluated by ten panelists (five men and five women) for smell when the shampoos were used.

TABLE 5

| Component | Amount (% by mass) |
|---|---|
| Sodium polyoxyethylene (3) lauryl ether sulfate | 25.0 |
| Lauryl amine oxide | 3.0 |
| Lauryl amine propyl betaine | 18.0 |
| Propylene glycol | 3.2 |
| Hydroxyethyl cellulose | 0.5 |
| 1,2-octanediol | 0.1 |
| Purified water | Remainder |

As a result of evaluating the smell of shampoo, nine panelists felt that the smell of the shampoo containing a 1,2-octanediol composition purified by the method described in Treatment 2 was better than that of the shampoo containing an untreated 1,2-octanediol composition; one panelist felt that the two shampoos have the same smell; and no panelist felt that the smell of the shampoo containing an untreated 1,2-octanediol composition was better than that of the shampoo containing a purified 1,2-octanediol composition.

The invention claimed is:

1. A process for producing an alkanediol composition, comprising the steps of:
   (a) oxidizing an olefin to produce an epoxy compound;
   (b) hydrolyzing the epoxy compound to produce the alkanediol composition; and
   (c) adding glycol compounds, or glycol compounds and water to the alkanediol composition and removing glycol compounds, or glycol compounds and water under reduced pressure.

2. The process for producing an alkanediol composition according to claim 1, wherein the alkanediol compound has a general formula (1),

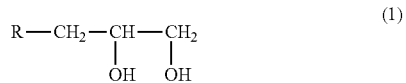

wherein R denotes an alkyl group having 4-15 carbon atoms.